United States Patent [19]
Koros et al.

[11] Patent Number: 5,236,436
[45] Date of Patent: Aug. 17, 1993

[54] REVERSE ACTION SURGICAL NEEDLE HOLDER

[76] Inventors: Tibor Koros; Gabriel Koros, both of 610 Flinn Ave., Moorpark, Calif. 93021

[21] Appl. No.: 699,420

[22] Filed: May 13, 1991

Related U.S. Application Data

[63] Continuation-in-part of Ser. No. 665,750, Mar. 7, 1991.

[51] Int. Cl.$^5$ ............................................. A61B 17/28
[52] U.S. Cl. ..................................... 606/148; 606/206; 606/208
[58] Field of Search ............... 606/206, 205, 148, 157, 606/208; 81/367, 380, 383

[56] References Cited

U.S. PATENT DOCUMENTS

| | | | |
|---|---|---|---|
| 1,359,164 | 11/1920 | Lo Gludice | 606/205 |
| 2,507,710 | 5/1950 | Grosso | 606/205 |
| 4,760,848 | 8/1988 | Hasson | 606/206 |

FOREIGN PATENT DOCUMENTS 2091624  8/1982  United Kingdom .............. 606/205

*Primary Examiner*—Michael H. Thaler
*Attorney, Agent, or Firm*—Jessup, Beecher, & Slehofer

[57] ABSTRACT

The surgical instrument is used to hold a suture needle and thread to suture a wound or incision on a patient. A pair of pivotal jaws form the bite area. A pair of pivot handles are placed in tandem to the pair of jaws. The front ends of the handles are pivotally connected to the back of the jaws. When the handles are at-rest, the jaws are shut. When the handles are squeezed together, the jaws open. There is a compression spring placed between the rear ends of the handle to keep tension on the handles to keep them spread apart, which in turn keeps tension on the jaws to keep them shut. The dual pivot points of the pair of handles and the pair of jaws increases the pressure at the bite of the jaws. The jaws remain closed and secure the needle to allow the surgeon to suture without having to keep tension on the handles keep the jaws shut. The surgeon squeezes the handles to temporarily open the jaws to release the needle or to grab the needle and then releases his grip on the handles. The surgeon can manipulate the instrument more easily.

2 Claims, 3 Drawing Sheets

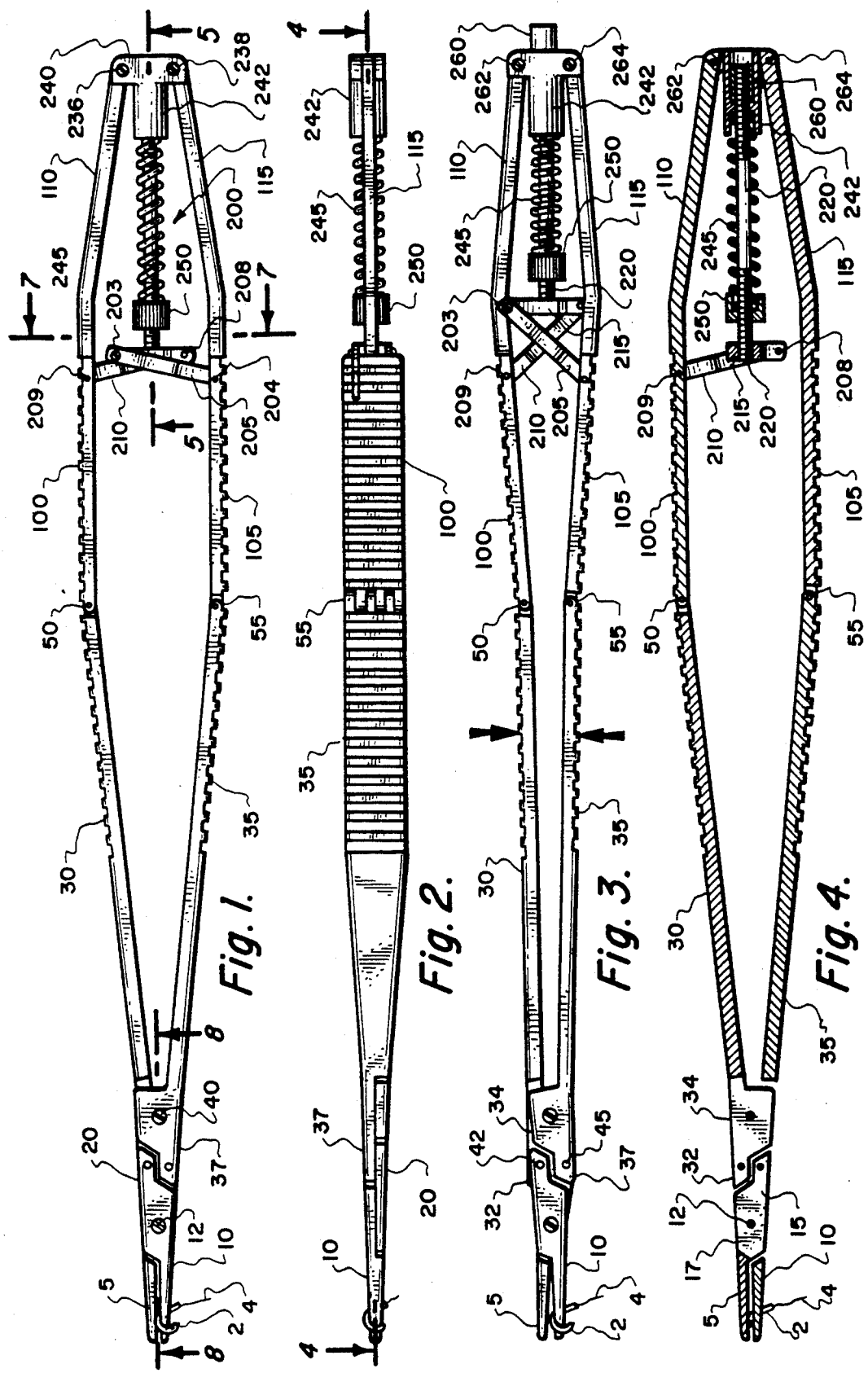

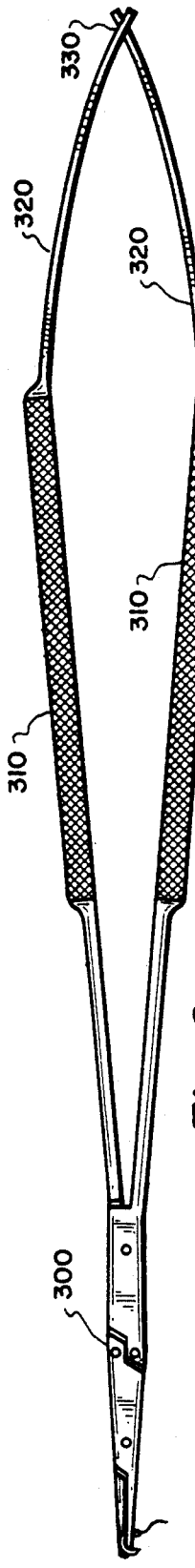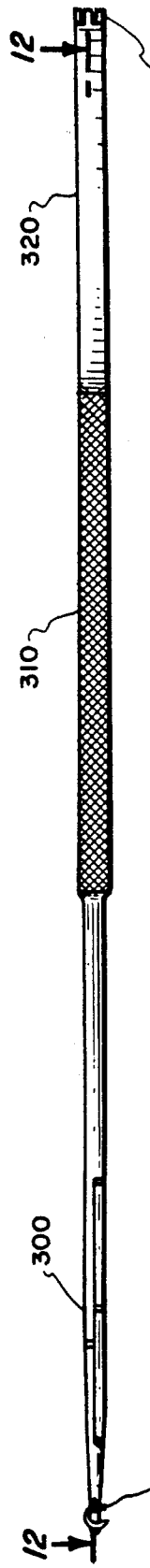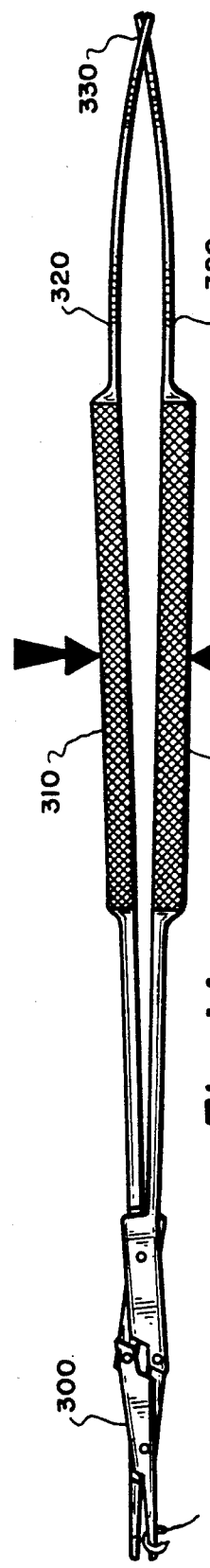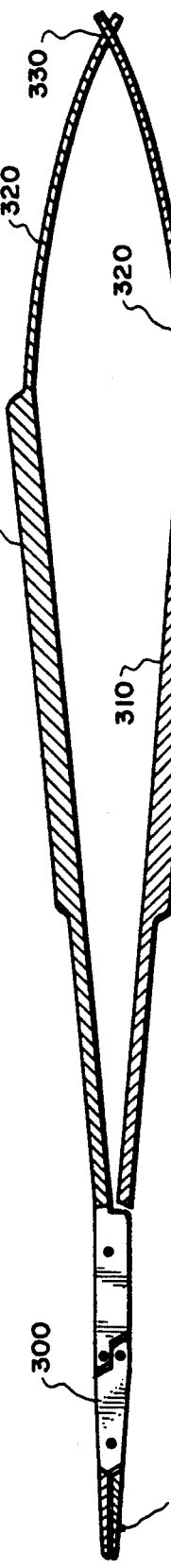

REVERSE ACTION SURGICAL NEEDLE HOLDER

CROSS REFERENCE TO RELATED APPLICATIONS

This is a continuation-in-part of application Ser. No. 07/665,750, which was filed on Mar. 7, 1991.

BACKGROUND OF THE INVENTION

1. Field of the Invention

Surgery: Medical and laboratory equipment: hand-held or manipulated surgical instrument or tool for medical or laboratory use; suture needle holder having jaws biased to the opened or closed position. Pair of tongs for holding a needle.

2. Description of the Prior Art

A conventional surgical needle holder or forceps is used by the surgeon who manipulates the handles to hold and work the surgical needle to suture the wound or incision on the patient. Conventional forceps are fabricated from a pair of rigid parts each having a jaw at one end and a handle with a ring at the other end. The two parts are mounted together to form a scissors-like instrument. The two parts are pivotally secured behind the pair of jaws. There is a finger ring and thumb ring at the distal end of each handle. The surgeon places his thumb in one ring and his index finger in the other ring to control and manipulate the forceps. He can squeeze the two rings together with his thumb and finger to cause the jaws to clamp down on the suture needle while at the same time moving the forceps to suture with the needle. The conventional forceps require squeezing while manipulating the forceps. Some forceps have engagable snap together locking means on the pair of handles and towards the rings to lock the jaws shut by locking the pair of handles together. It is usually a snap connection. The lock will engage when sufficient force is supplied by the finger and thumb to press the rings together. The lock will disengage when sufficient force is applied to spread apart the rings.

SUMMARY AND OPERATION OF THE INVENTION

The surgical instrument is used to hold a suture needle and thread to suture a wound or incision on a patient. A pair of pivotal jaws form the bite area. A pair of pivot handles are placed in tandem to the pair of jaws. The front end of the handles are pivotally connected to the back of the jaws. When the handles are at-rest, the jaws are shut. When the handles are squeezed together, the jaws open. There is a compression spring placed between the rear ends of the handle to keep tension on the handles to keep them spread apart, which in turn keeps tension on the jaws to keep them closed and pressing against each other. The dual pivot points of the pair of handles and the pair of jaws increases the pressure at the bite of the jaws. The jaws remain closed and secure the needle to allow the surgeon to suture without having to keep tension on the handles to keep the jaws shut. The surgeon squeezes the handles to temporarily open the jaws to release the needle or to grab the needle and then releases his grip on the handles. The surgeon can manipulate the instrument more easily.

The present invention is a double action surgical needle holder. The pair of scissor jaws which come together to grip the needle is conventional in nature. The pair of jaws have jaw ends at the tip and opposite attachment ends. They are pivotally connected so that they can have a scissors-like action. There are a pair of opposite spaced apart angularly disposed handles also pivotally connected toward their first ends so that the pair of handles will move in a scissor-like fashion. The proximal first ends of the pair of handles are pivotally connected to the attachment ends of the jaws so that there can be movement where the pair of handles connect to the attachment ends of the pair of jaws.

By having this double pivoting action, the surgical instrument works in just the opposite fashion from the conventional surgical instruments known in the prior art. In the at-rest position, the jaws are normally closed. The surgeon squeezes the handles together to open up the jaws and to place the suture needle in the bite of the jaws. By releasing the squeezing grip on the handles, the jaws will close shut on the needle and secure it without requiring the surgeon to continuously squeeze and press the handles together. The surgeon is free to manipulate the needle holder without keeping the tension to hold the jaws shut. It works opposite way from a typical needle holder where the surgeon squeezes the handles to hold the needle while suturing and then opens the handles to release the suturing needle. The present invention allows the surgeon to suture without having to keep tension on the instrument itself. The distal or rear portion of the present invention has a tension adjusting means so that the amount of tension placed at the closure or bite of the jaw can be adjusted to an individual surgeon's tactile feelings. However, the main purpose for the tension adjusting means is to allow the present invention to be used in a variety of surgical procedures. Surgical needles come in various sizes and are used for particular surgical procedures. Small needles, called "fine" size, are labeled 6.0 to 8.0 in the surgical supply industry. "Fine" sized surgical needles with their attached threads are used in open heart and other cardiovascular surgery. "Micro" sized needles are labeled 8.0 to 10.0 in the surgical supply industry. "Micro" needles are used during microsurgery such as eye surgery and plastic surgery. Microsurgery is often done with the aid of a telescope. The surgeon views through the telescope while suturing. The "fine" and "micro" surgical needles are bow-shaped and can be bent if they are squeezed too hard in the jaws of the present invention. A bent needle is unacceptable to the surgeon. The tension adjusting means allows the surgeon to adjust the tension at the bite of the jaws so that the instrument can be used for micro or fine surgery. The surgeon can "fine tune" the tension at the bite of the jaws so that the particular needle used is held firmly in the jaws while the surgeon is suturing without deforming the surgical needle. The adjustment means is illustrated in one embodiment by a toggle joint connected between two parallel opposed sides which are hingedly connected to the rear of the disposed handles. The toggle joint keeps the handles spread apart at the at-rest position unless the surgeon squeezes together the handles. In turn, the toggle joint has a male screw or threaded rod which is medially positioned along the longitudinal axis of the needle holder. The male screw is threaded to a female screw or cylindrical nut placed in the T-shaped joint located at the distal end of the instrument. The T-shaped joint is pivotally secured to the rear of the hinged sides. There is a barrel portion aligned also along the medial longitudinal axis of the surgical instrument. The male screw is in alignment with the barrel and the female screw within the barrel. The female screw holds the male screw. The male screw can be turned by a knurled adjustment nut secured to the proximal end of the male screw so that if the knurled nut is turned, the male screw will rotate a the same amount. The male screw, the female screw and the adjustment nut all rotate as a unit. By turning the male screw, the coil spring is compressed or expanded between the adjustment nut and the T-shaped joint. This changes the tension between the hinged sides. The spring tension is placed against the toggle joint and causes a squeezing or pinching force in the bite of the pair of jaws. The female screw initially sets the angle of the toggle joint arms. This angle can be preset at the factory and then sealed off in the barrel.

In the other variant of the invention, instead of having a toggle joint and hinged sides, the handles have an integral pair of bow-shaped springs that hook together at their distal ends to form a wishbone-like rear portion appearance. When the springs are hooked together, they create a bent spring to create a squeezing force in the bite of the pair of jaws. The two ends have slits so that the two ends can be hooked together and unhooked if desired. When they are hooked together the tension is created on the double pivot action to keep the bite of the jaws closed. This version precludes any adjustment of the tension because it is set when the handles are fabricated. However, by fabricating different thicknesses of the spring or the way that they are angled will result in different tensions being exerted on the bite of the jaw area.

BRIEF DESCRIPTION OF THE DRAWINGS

FIG. 1 is a top plan view of the invention;

FIG. 2 is a left side elevational view of the invention, the right side being identical to the left side after the invention is rotated 180 degrees about its medial longitudinal axis:

FIG. 3 is a top plan view of the invention showing the hinged sides compressed and the jaws of the needle holder open;

FIG. 4 is a sectional view taken along the line 4—4 of FIG. 2.

FIG. 9 is a top plan view of a variant of the invention.

FIG. 10 is a left side elevational view of the variant of the invention, the right side view being identical to the left side after the invention is rotated 180 degrees about its medial longitudinal axis.

FIG. 11 is a top plan view of one variant of the invention showing the sides and tension adjustment portion compressed and the needle holder open.

FIG. 12 is a sectional view taken along the line 12—12 of FIG. 10.

DETAILED DESCRIPTION OF THE INVENTION

Figure 8:
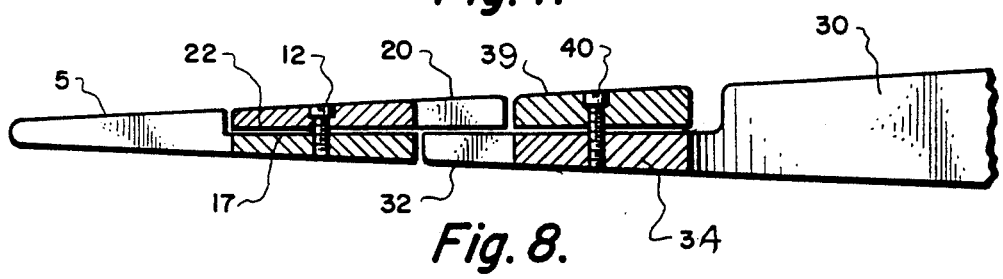
FIG. 8 is a partial sectional view of the tip of the invention taken along the line 8—8 of FIG. 1.

The invention will now be described in detail. FIGS. 1-8 illustrate the present invention having hinged sides and a toggle joint. FIGS. 1-8 illustrate the suture needle 2 and suture thread 4 grasped in the bite of the pair of jaws 5 and 10. FIG. 1 illustrates the top plan view of the present invention. This view clearly illustrates the pair of jaws at the tip or proximal end, the pair of tandem handles behind the jaws, the pair of legs, the T-joint at the distal end, and the toggle joint mounted between the pair of legs or hinged links. There is disclosed the proximal or jaw tip end showing the pair of opposed jaws labeled 5 and 10 which are mounted face to face and on top of each other in an opposed arrangement The pair is pivotally connected together with a small jeweler's screw 12. The two halves that form the pair of jaws are identical to each other. One side of each jaw half has a shelf or flat portion toward its distal end. The flat portion on jaw 5 is labeled 17, and the flat portion on jaw 10 is labeled 22. The pair of jaws are mounted together so that both flat portions 17 and 22 face each other and can rub together when the jaws pivot. This is clearly illustrated in FIG. 8. The flat portion 17 of jaw 5 is illustrated in FIG. 4. The two distal attachment ends 15 and 20 of the pair of jaws have a pair of angularly positioned handles labeled 30 and 35 attached to both of them. The pair of handles 30 and 35 are also pivotally connected together by a small jeweler's screw 40 located toward their first or proximal ends 32 and 37. The pair of handles 30 and 35 are positioned in a tandem relationship with the pair of jaws 5 and 10. Both handles 30 and 35 are identical to each other and are mounted face to face and on top of each other in an opposed arrangement. One side of each handle has a flat portion toward its proximal end. The pair of handles are mounted together so that both flat portions 34 and 39 face and touch each other. The flat portion 34 of handle 30 is illustrated in FIG. 4. The distal or attachment ends 15 and 20 of the pair of jaws 5 and 10 each has a flat portion 17 and 22 that overlies the distal end of the pair of handles. The two attachment ends 32 and 37 of the handles each has a flat portion 34 and 39. The two attachment ends of the pair of jaws overlie the attachment ends of the pair of handles. Both connections are each held together by pivot pins 42 and 45. This creates a pivotal connection where each jaw end and handle end are linked together. The attachment end 20 of jaw 10 is pivotally connected to the attachment end 32 of handle 30 with pivot pin 42. The attachment end 15 of jaw 5 is pivotally connected to the attachment end 37 of handle 35 with pivot pin 45. When the pair of handles 30 and 35 are squeezed together, the jaws are open, as illustrated in FIG. 3. When the handles not squeezed together, the jaws are closed as illustrated in FIG. 1. The tip portion is shown in an enlarged sectional view in FIG. 8 illustrating how the pair of jaws are pivotally secured together by a small jeweler's screw 12 and the tandemly positioned ends of the angular handles are also pivotally secured by the second small jeweler's screw 40.

The transverse distal portion of the hinged needle holder as shown in FIG. 1 further illustrates a pair of opposed rigid legs labeled 100 and 105. The end portions of these two bowed legs are interconnected by a T-shaped joint 240. The two opposed legs 100 and 105 are hingedly connected to the distal ends of the two handles 30 and 35 by means of hinge joints 50 and 55, the left side of which can be clearly seen in the side elevational view in FIG. 2. Each hinge connection between the handles and the bowed leg portions 100 and 105 allows the two opposed handles 30 and 35 to be compressed or otherwise squeezed together as shown in FIG. 3. This squeezing action in turn will open up the pair of opposed jaws 5 and 10 to allow the surgeon to release the suture needle held in the bite or pincers of the jaws. The pair of pivoted jaws 5 and 10 and the angularly positioned pair of handles 30 and 35 allow for a double tensioning to keep the bite or grip of the jaws shut. This multiplication of the force or pressure put on the tip of the pair of jaws 5 and 10 is achieved by this double action. The two pivot points increase the squeezing pressure on the tips of the pair of opposed jaws 5 and 10. This results in a reverse action so that the bite of the jaws 5 and 10 is closed unless and until the surgeon squeezes or compresses the hinged sides. This is exactly the opposite operation of the conventional surgical needle holder or forceps where the surgeon manipulates the handles to hold and work the surgical needle to suture the wound or incision on the patient. The conventional forceps are fabricated from a pair of rigid parts each having a jaw at one end and a handle with a ring at the other end. The two parts are mounted together to form a scissors-like action. The two parts are pivotally secured behind the pair of jaws. There is a finger ring and thumb ring at each distal end of the handles. The surgeon places his thumb in one ring and his index finger in the other ring to control and manipulate the forceps. He can squeeze the two rings together with his thumb and finger to cause the jaws to clamp down on the suture needle while at the same time moving the forceps to suture with the needle. The conventional forceps require squeezing while manipulating the forceps. Some forceps have engageable snap together locking means on the pair of handles and towards the rings to lock the jaws shut by locking the pair of handles together. It is usually a snap connection. The lock will engage when sufficient force is supplied by the finger and thumb to press the rings together. The lock will disengage when sufficient force is applied to spread apart the rings.

In the present invention, tension or force is maintained between the hinged sides to keep them spaced apart and to prevent them from being squeezed together unless sufficient force is exerted by the surgeon by squeezing the sides between the thumb and the index finger. The tension is maintained and can be adjusted by a toggle joint 200, which is clearly shown in the plan view in FIG. 1. The toggle joint is also shown in the enlarged views in FIGS. 5-7.

The toggle joint has two arms 205 and 210 jointed together at their inner ends to an intermediate transverse bar 215. The outer ends of the arms 205 and 210 are hingedly connected to the legs 100 and 105. When the hinged sides of the present invention are squeezed together, the pair of arms 205 and 210 will also bend to compensate for the reduced space in between the two sides. This action is illustrated in FIG. 3 where it shows both arms angularly extending distally. The transverse are 215 has one end of a rod secured to it. The rod is threaded at both ends. The rod can be described as a male screw 220 that interconnects the bar 215 and the T-joint 240. The T-joint holds together the distal ends of the pair of legs 100 and 105 in a hinged fashion. The male screw 220 is axially positioned in a coil compression spring 245. The screw 220 is longer than the spring 245. There is a tension adjusting female nut 260 threadably engaged to the male screw 220 towards the distal end of the screw. The proximal end of the male screw 220 is secured to the bar 215 of the toggle joint to mount the screw and to prevent the screw from turning. The other end of the threaded rod or male screw 220 is threadably engaged to the cylindrical female screw 250 positioned inside the T-joint 240. The T-joint 240 has a central barrel 242 which is aligned with the medial longitudinal axis of the present invention. The barrel 242 has a bore and an annular retaining ring 244 positioned just inside the mouth of the bore toward the proixmal end. The annular ring. and the mouth of the bore act as a stop and a seat for the end of the spring. Alternatively, the diameter of the spring can be the same as rim of the barrel so that the distal end of the spring abuts against the end of the barrel to function as a stop. The annular ring 244 also acts as a stop for the female screw. It keeps the female screw 260 in the bore of the barrel. By turning the adjustment nut 250 one way, the nut threads itself towards the mouth of the barrel of the T-joint and will compress the tension spring resulting in more tension exerted at the toggle joint to give greater squeezing force at the bite of the pair of jaws 5 and 10. The female screw is used to adjust he angle of the toggle arms. The female screw shortens or lengthens the effective distance between the cross bar 215 and the T-joint. The side elevation of FIG. 2 illustrates distal or rear portions 110 and 115 of the two legs being flat rigid braces to allow both arms 205 and 210 of the toggle joint to bend above and below the braces when the hinged sides are compressed by the surgeon.

By turning knob 250, the surgeon can adjust the compression force at the bite of the jaws. This allows the instrument to accommodate various sizes of suture needles. This eliminates the need for multiple instruments each designed to be used with a single type of suture needle.

Figure 5:
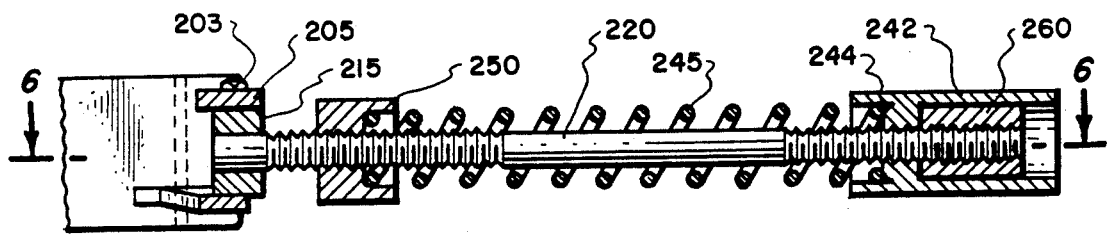
FIG. 5 is a partial sectional view of the base of the invention taken along the line 5—5 of FIG. 1.
Figure 6:
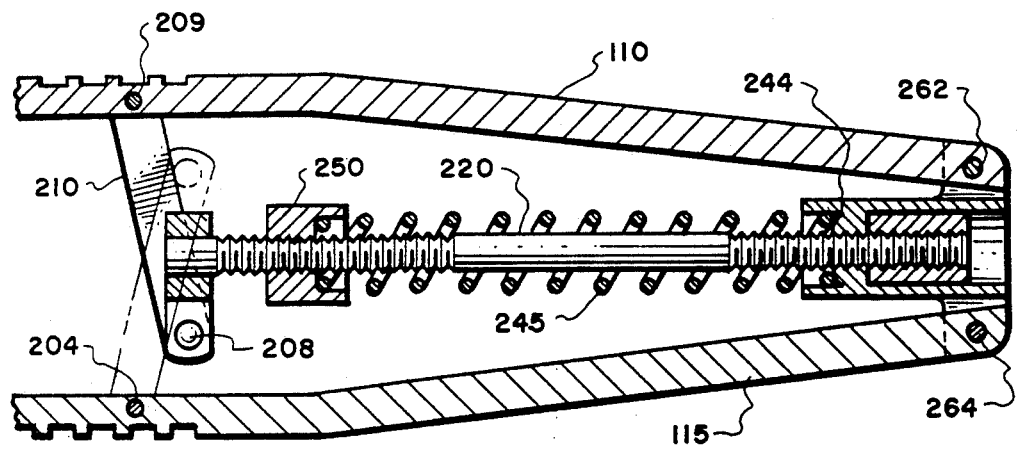
FIG. 6 is a partial sectional view taken along the line 6—6 of FIG. 5.
Figure 7:
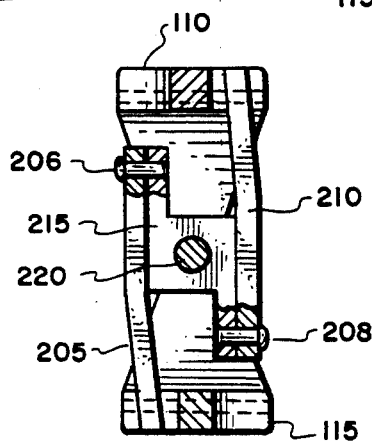
FIG. 7 is a cross-sectional view taken along the line 7—7 of FIG. 1.

FIGS. 5 and 6 are enlarged views showing the relationship between the toggle joint 200, the T-bar joint 240, the threaded rod or male screw 220, the coiled compression spring 245, the adjustment nut 250, and the cylindrical female screw 260 located within the barrel of the T-joint. As can be seen in this enlargement, the turning of the adjustment nut 250 will compress or extend the compression spring to change the tension resulting on the two toggle arms 205 and 210. The female screw 260 extends from the distal end of the barrel when the hinged sides are squeezed together. The female screw can be turned to adjust the angles of the toggle arms 205 and 210 relative to the hinged sides. Once the female screw is initially adjusted, further adjustments are not necessary. The female screw can be preset at the factory and sealed off to prevent tampering with the adjustment later on.

The present invention is also designed to minimize the number of different parts that are required. The pair of jaws are identical. The pair of handles are identical. The pair of bowed legs are identical. The pair of arms on the toggle joint are identical. The two jeweler's screws for the pivot connections are identical. The two pivot pins that hold the handles to the legs are identical. The pivot pins that secure the toggle arms to the legs are identical. The pivot pins that secure the arms to the transverse bar are identical. In the variant, the pair of jaws are identical and the pair of handles are identical.

FIGS. 9-12 show a variant of the invention where the hinged sides and the toggle joint adjustments are replaced with two bow shaped extensions from the knurled handles and which c an be hooked together at their distal ends to form a tension spring to keep the angularly positioned handles spread apart and tensioned. The proximal portion of the invention up to the knurled handle area begins is functionally identical to that previously discussed with regard to FIGS. 1-8. There is the pair of jaws 300 and the pair of angularly shaped handles 310 which are pivotally connected and which are connected in tandem to the pair of jaws to have a double pivot action resulting in a reverse action at the opening of the jaws. The resulting wishbone-shaped ends 320 of the handles function as a spring to keep the two handles 310 spread apart and therefore the jaws closed and tightly holding the needle as shown in FIGS. 9 and 10. By squeezing together the two handles as shown in FIG. 11 and the jaw tips open to allow the surgeon to release the suture needle in he bite of the jaw area. This variance has no means to adjust the squeezing force at the bite of the pair of jaws 300. However, the tension could be changed by changing the stiffness in the two wishbone-like springs when the surgical instrument is fabricated. There are a pair of hooks 330 at the distal ends of the handles. The ends can hooked and unhooked by bending the wishbone portions 320.

Whereas the present invention has been shown and described herein in what is conceived to be the best mode contemplated, it is recognized that departures may be made therefrom not to be limited to the details disclosed herein but is to be afforded the full scope of the invention.

What is claimed is:

1. A Reverse Action Surgical Needle Holder comprising:
   a pair of scissor jaws having jaw ends and attachment ends and pivotally secured to each other with a pivot pin, said jaw ends being used for grasping a surgical needle and thread;
   a pair of spaced apart angularly opposed handles having first ends and second ends, said handles being pivotally secured together towards said first ends, said first ends being pivotally secured to and in tandem with said attachment ends of said pair of scissor jaws;
   tensioning means hingedly secured to said second ends of said handles for keeping said jaws closed and said opposed handles spread apart when at the at-rest position, said tensioning means allowing said handles to be compressed by the surgeon to open said pair of jaws; and
   said tensioning means compresses a pair of spaced apart opposed hinged links having first ends and second ends, said first ends being hingedly secured to said second ends of said pair of handles.

2. A Reverse Action Surgical Needle Holder comprising:
   a pair of scissor jaws having jaw ends and attachment ends and pivotally secured to each other with a pivot pin, said jaw ends being used for grasping a surgical needle and thread;
   a pair of spaced apart angularly opposed handles having first ends and second ends, said handles being pivotally secured together towards said first ends, said first ends being pivotally secured to and in tandem with said attachment ends of said pair of scissor jaws;
   tensioning means hingedly secured to said second ends of said handles for keeping said jaws closed and said opposed handles spread apart when at the at-rest position, said tensioning means allowing said handles to be compressed by the surgeon to open said pair of jaws; and
   said tensioning means compresses a toggle joint.

* * * * *